(12) United States Patent
Zavadtsev et al.

(10) Patent No.: US 8,734,717 B2
(45) Date of Patent: *May 27, 2014

(54) STERILISATION OF LIQUIDS IN HERMETICALLY CLOSED VESSELS

(75) Inventors: Aleksandr Zavadtsev, Reutov (RU); Pavel Koulik, Blaesheim (FR)

(73) Assignee: Opus Industry SA, Yverdon (CH)

(*) Notice: Subject to any disclaimer, the term of this patent is extended or adjusted under 35 U.S.C. 154(b) by 802 days.

This patent is subject to a terminal disclaimer.

(21) Appl. No.: 12/450,257

(22) PCT Filed: Mar. 20, 2008

(86) PCT No.: PCT/IB2008/000671
§ 371 (c)(1),
(2), (4) Date: Apr. 21, 2010

(87) PCT Pub. No.: WO2008/114136
PCT Pub. Date: Sep. 25, 2008

(65) Prior Publication Data
US 2011/0123690 A1    May 26, 2011

(30) Foreign Application Priority Data
Mar. 21, 2007 (EP) .................................... 07005762

(51) Int. Cl.
*A61L 2/00* (2006.01)
*A01N 1/00* (2006.01)
*A23L 3/00* (2006.01)
*C12H 1/06* (2006.01)
*C12H 1/08* (2006.01)
*C12H 1/18* (2006.01)

(52) U.S. Cl.
CPC ... *A01N 1/00* (2013.01); *A23L 3/00* (2013.01); *A61L 2/00* (2013.01); *C12H 1/06* (2013.01); *C12H 1/08* (2013.01); *C12H 1/18* (2013.01)
USPC .............................................. 422/22; 422/38

(58) Field of Classification Search
CPC .............. A01N 1/00; A23L 3/00; A61L 2/00; C12H 1/06; C12H 1/08; C12H 1/18
USPC ...................................................... 422/22, 38
See application file for complete search history.

(56) References Cited

U.S. PATENT DOCUMENTS 3,272,636 A    9/1966    Isaac et al.
4,346,650 A *  8/1982    Zaitsu ............................. 99/361

(Continued)

FOREIGN PATENT DOCUMENTS

| EP | 1 328 167 | 10/2006 |
|----|-----------|---------|
| WO | WO 00-56179 | 9/2000 |
| WO | WO 02/34075 A1 | 5/2002 |

OTHER PUBLICATIONS

English Translation of International Preliminary Report on Patentability issued by the Bureau international de l'OMPI, Geneva, Switzerland, dated Sep. 22, 2009 for International PCT Application No. PCT/IB2008/000671; 6 pages.

(Continued)

*Primary Examiner* — Monzer R Chorbaji
(74) *Attorney, Agent, or Firm* — Faegre Baker Daniels LLP

(57) ABSTRACT

A process for the sterilization of hermetically sealed containers containing a liquid to be sterilized, comprising transport of the containers to a treatment zone where the containers are immersed in a flux of external fluid, the heating in volume of the liquid to be sterilized by electromagnetic waves at a rate greater than 28° C. per second to a treatment temperature T of between 20° C. and 66° C., agitation of the container during heating of the liquid, and dependant on the value of the treatment temperature T, exposure of the liquid to an alternating electric field in pulses immediately or slightly after heating of the liquid.

9 Claims, 17 Drawing Sheets

(56) References Cited

U.S. PATENT DOCUMENTS

| | | | |
|---|---|---|---|
| 4,695,472 | A | 9/1987 | Dunn et al. |
| 5,048,404 | A | 9/1991 | Bushnell et al. |
| 5,235,905 | A | 8/1993 | Bushnell et al. |
| 5,290,583 | A | 3/1994 | Reznik et al. |
| 6,093,432 | A * | 7/2000 | Mittal et al. .................. 426/237 |
| 6,626,087 | B2 * | 9/2003 | Roumagnac .................... 99/330 |
| 2004/0005242 | A1 | 1/2004 | Koulik et al. |
| 2004/0084381 | A1 | 5/2004 | Korenev |

OTHER PUBLICATIONS

European Search Report issued by the European Patent Office, dated Sep. 5, 2007, for European patent application No. EP07005762; 2 pages.

English Translation of International Search Report, issued by the European Patent Office, dated Aug. 20, 2008, for International PCT Application No. PCT/IB2008/00619; 6 pages.

English Translation of International Preliminary Report on Patentability issued by the Bureau international de l'OMPI, Geneva, Switzerland, dated Sep. 22, 2009 for International PCT Application No. PCT/IB2008/000619; 5 pages.

Mertens, Bart and Knorr, Dietrich, "Developments of Nonthermal Processes for Food Presevation," 156 Food Technology, May 1992, No. 5., pp. 124 and 126-133.

Search Report for Application No. PCT/IB2008/000671, 5 pages.

Written Opinion (and English translation) issued by the European Patent Office, Rijswijk, NL, dated Sep. 16, 2008, for International PCT Application No. PCT/IB2008/000671; 10 pages.

Written Opinion (and English translation) issued by the European Patent Office, Munich, Germany, dated Aug. 20, 2008, for International PCT application No. PCT/IB2008/000619; 9 pages.

International Search Report (and English translation), issued by the European Patent Office, Rijswijk, NL, dated Sep. 16, 2008, for International PCT Application No. PCT/IB2008/000671; 7 pages.

* cited by examiner

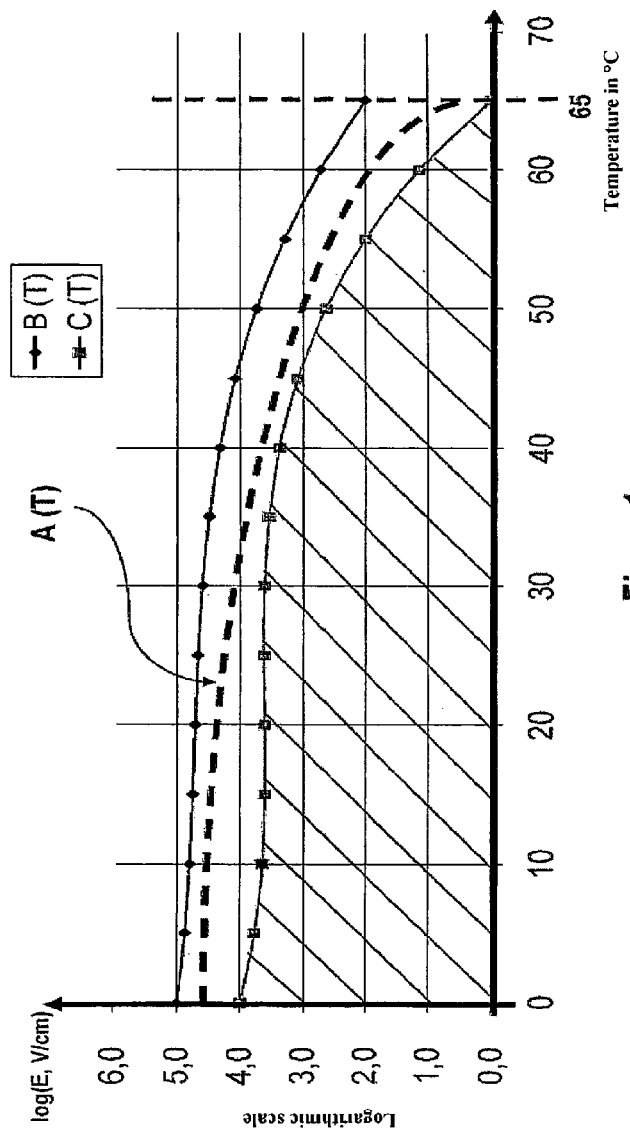
-Figure1-

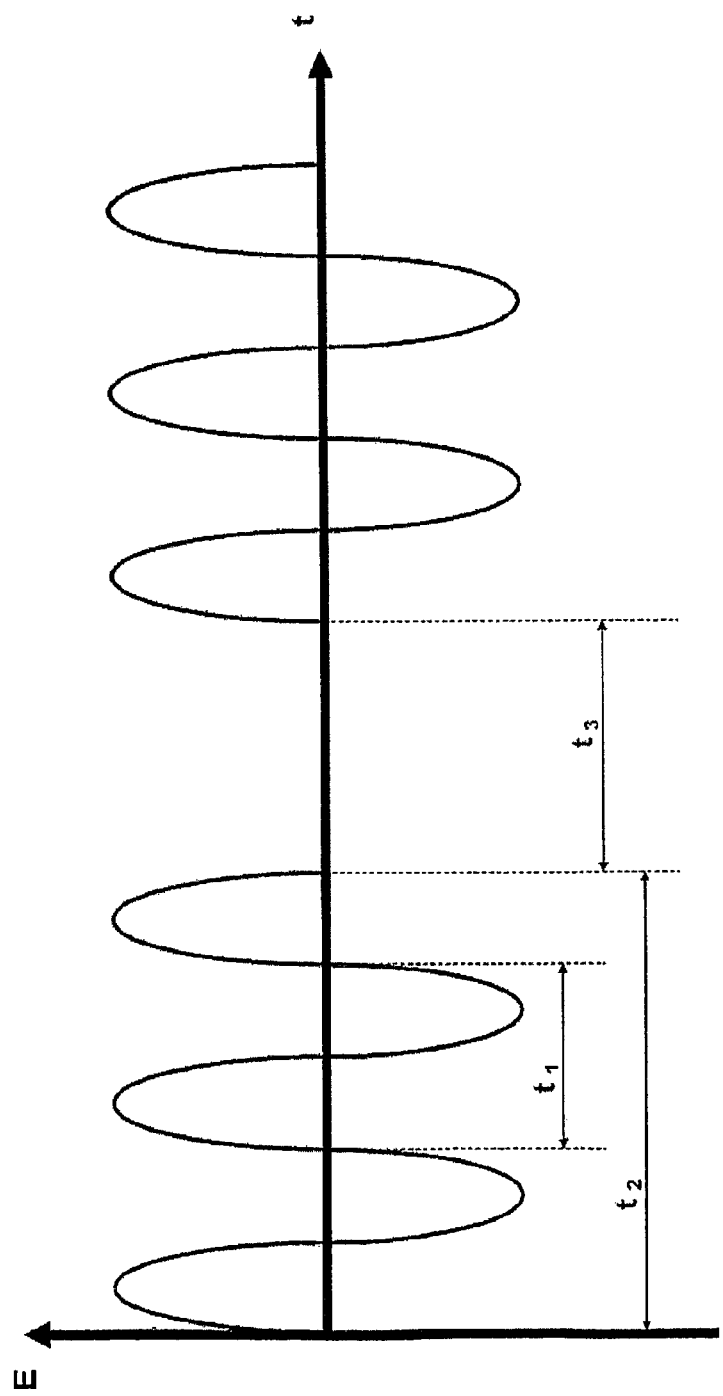
- Figure 2 -

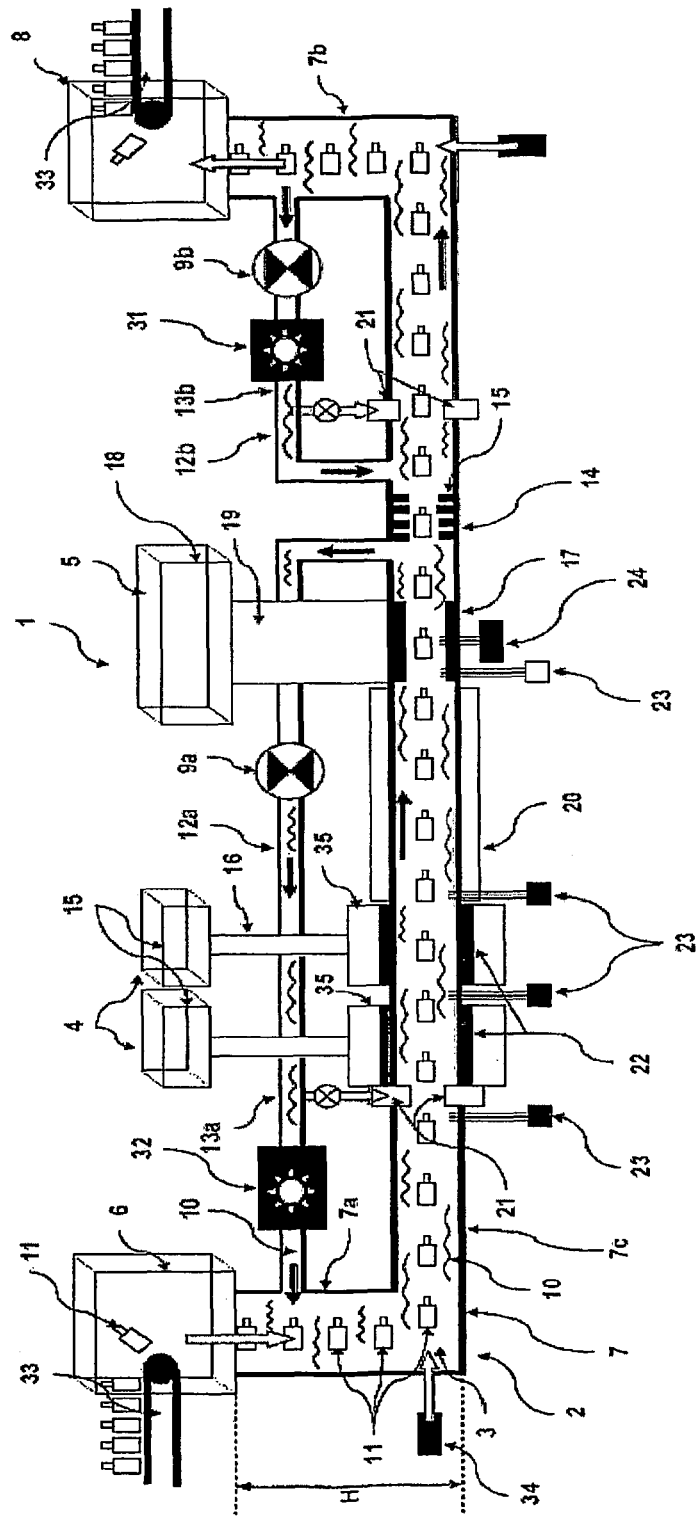
- Figure 3 -

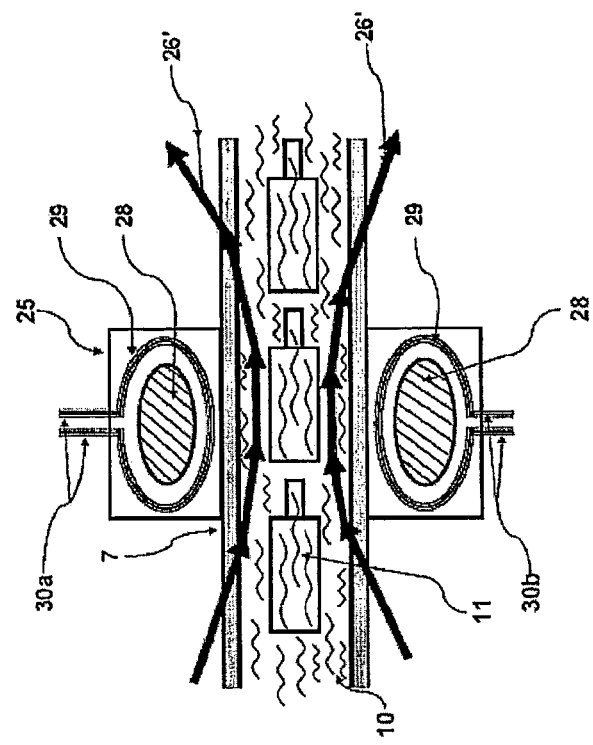
- Figure 4b -
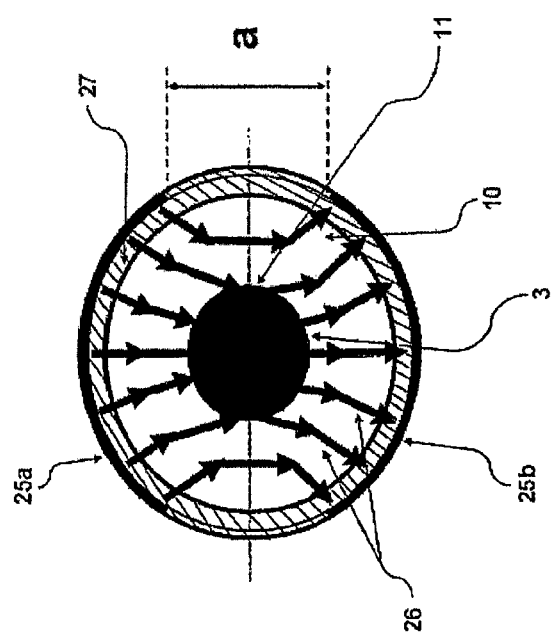
- Figure 4a -

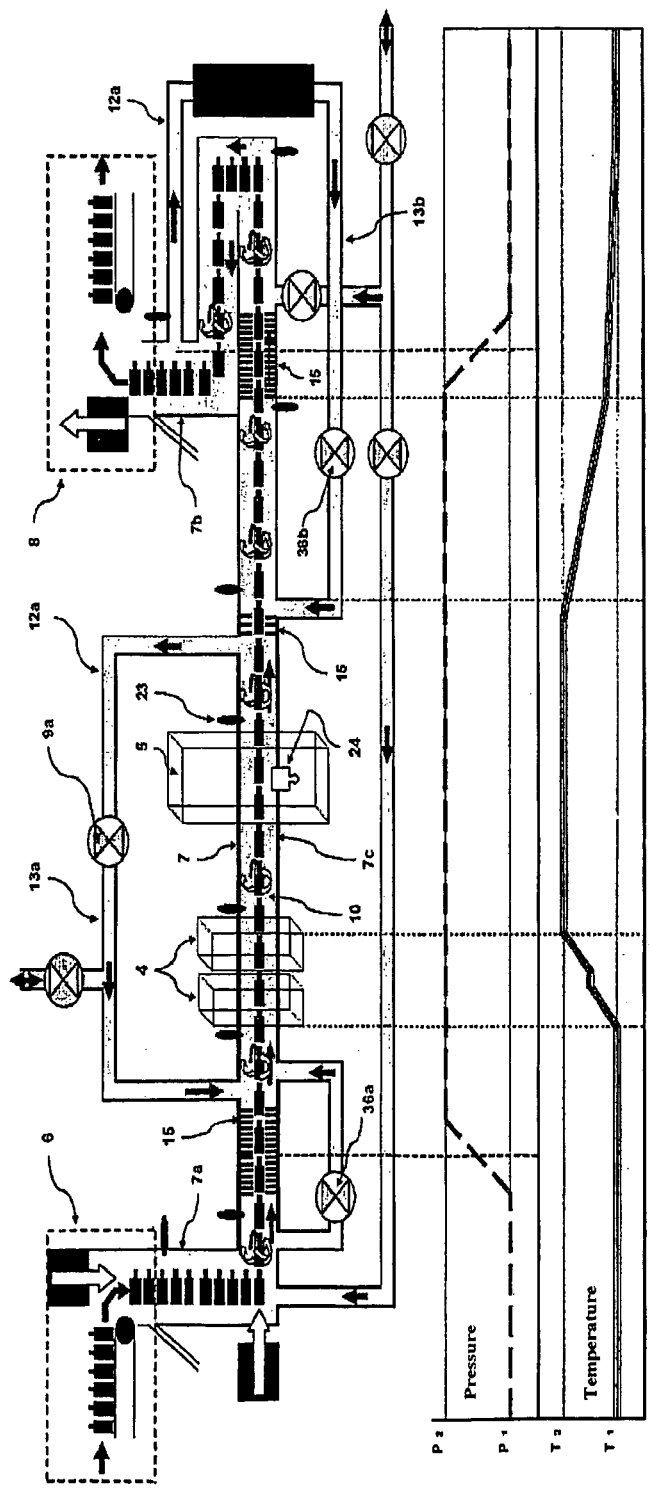
-FIGURE 5-

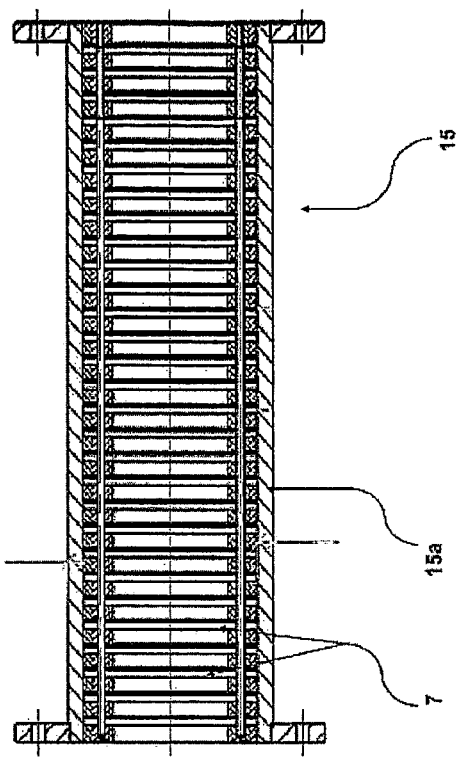
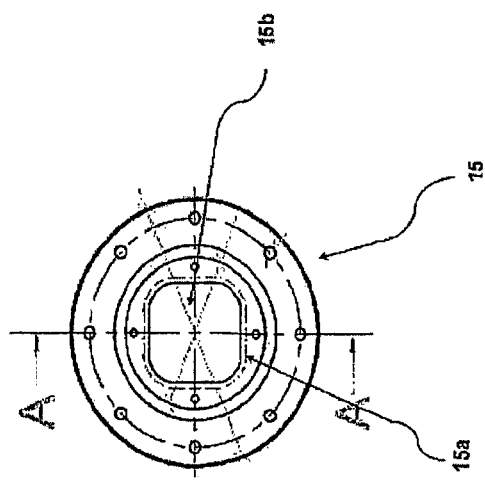
- Figure 6b -
- Figure 6a -

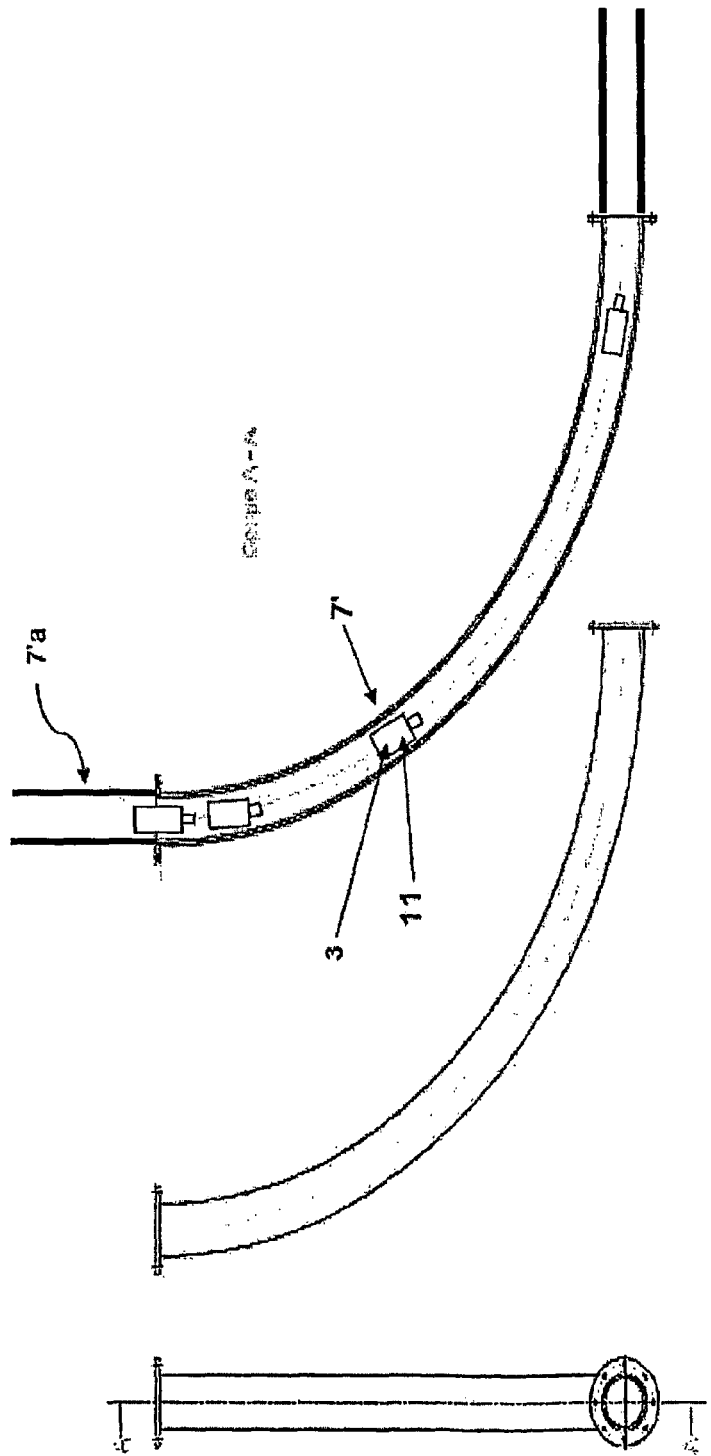
- Figure 7 -

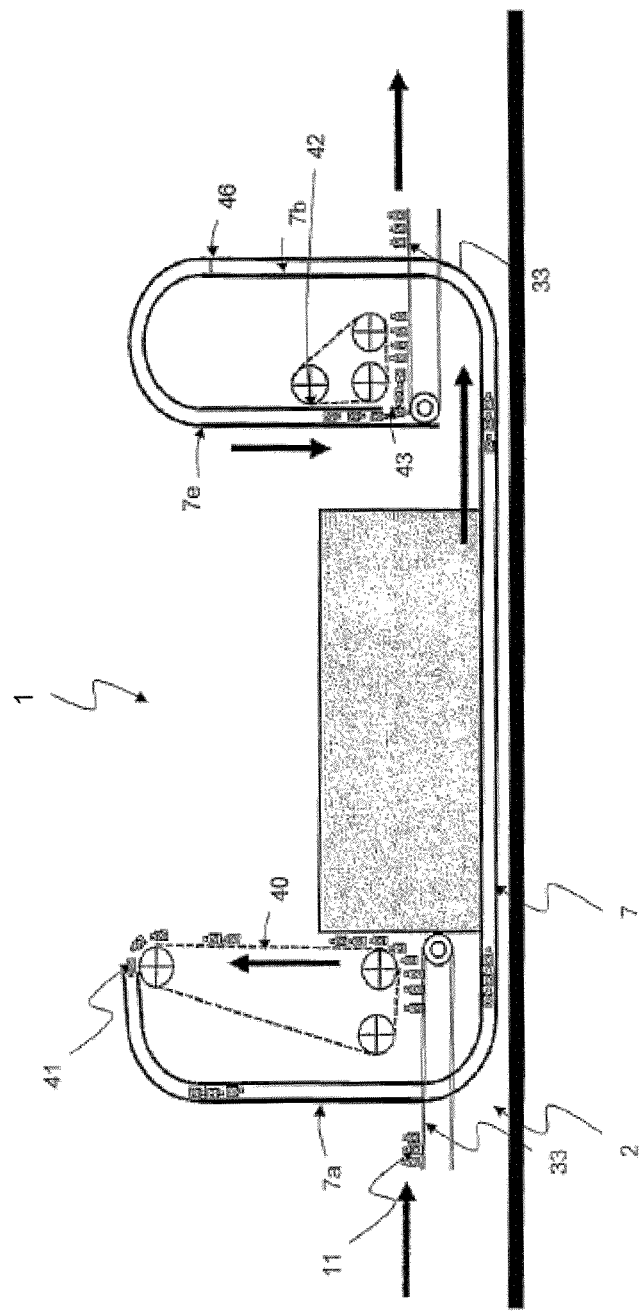

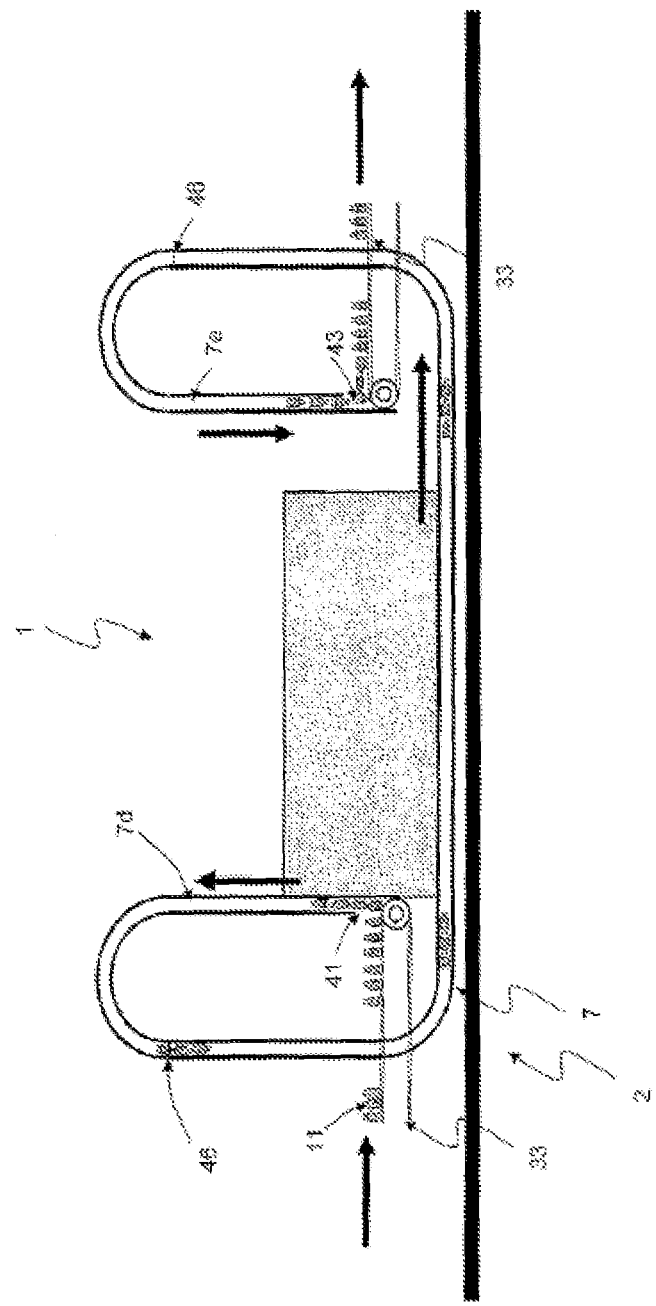

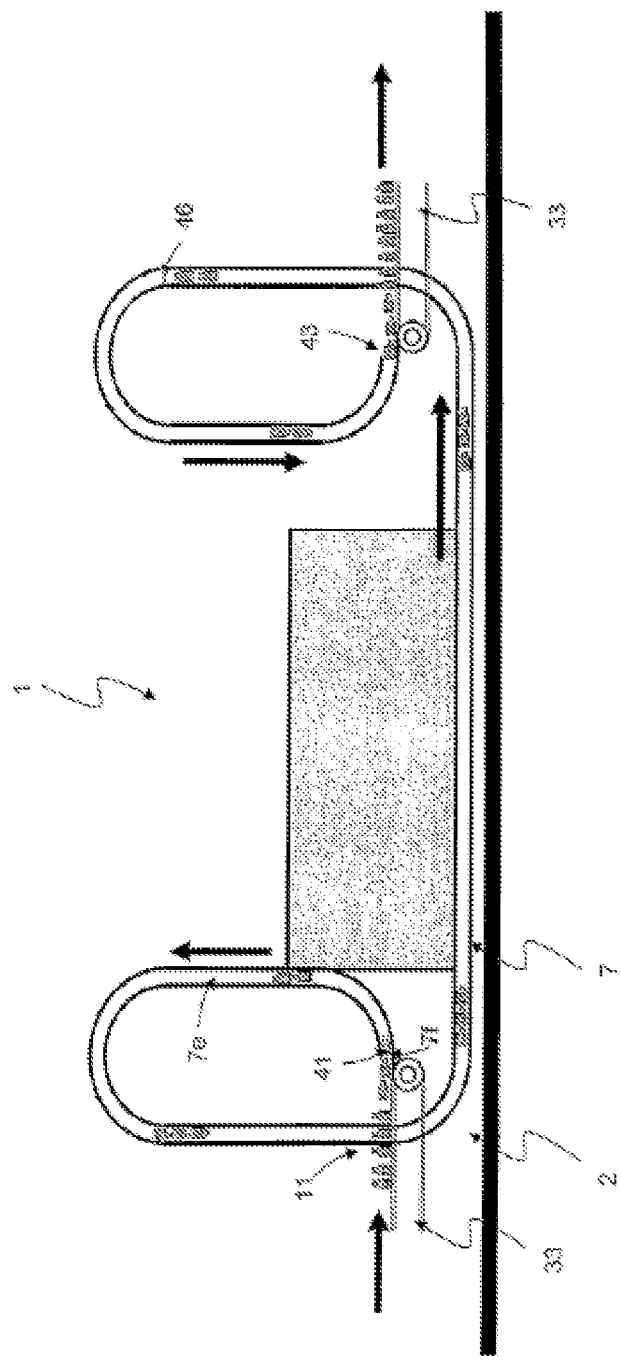

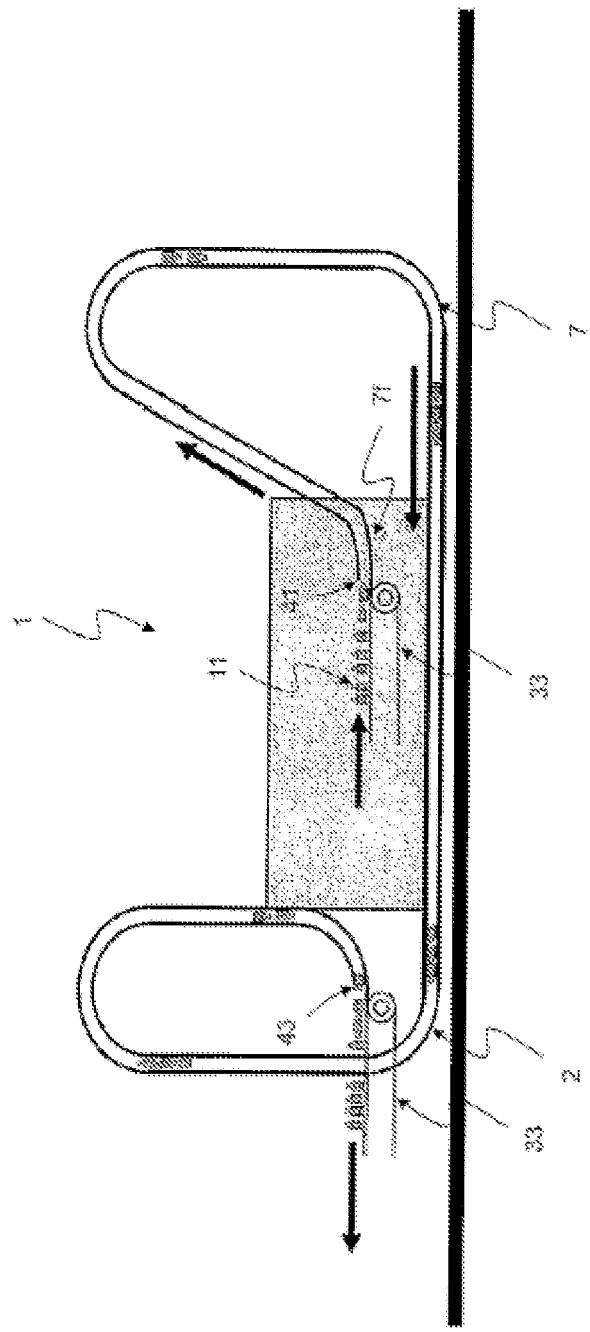

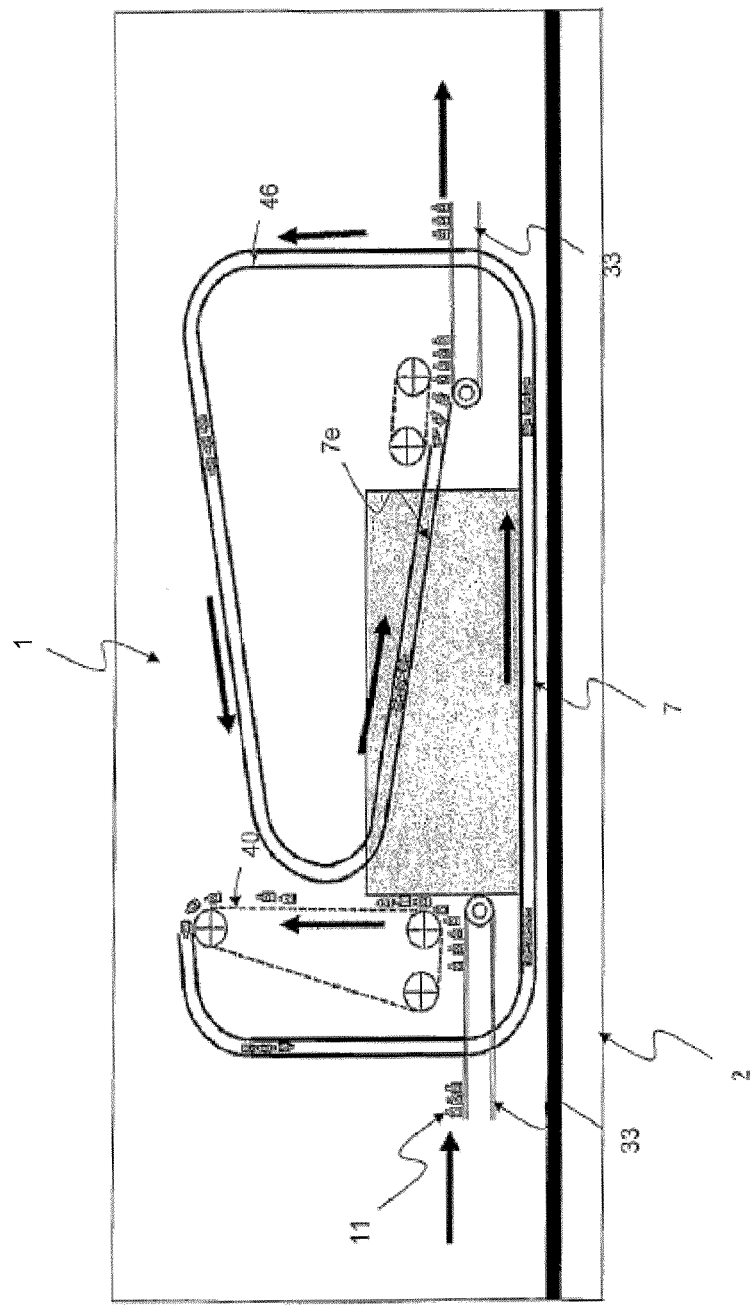

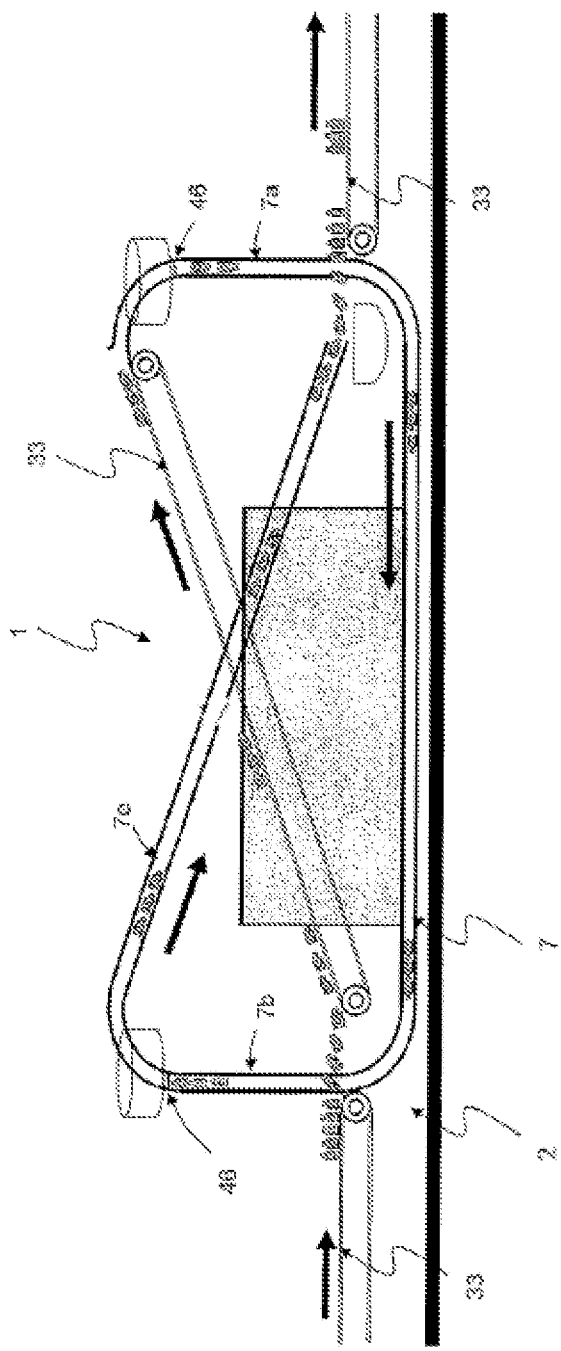

STERILISATION OF LIQUIDS IN HERMETICALLY CLOSED VESSELS

CROSS-REFERENCE TO RELATED APPLICATION

This application is a National Stage filing of PCT International Application Serial No. PCT/IB2008/000671, filed Mar. 20, 2008, which claims the benefit of European Application Serial No. EP 07 005 762.5, filed Mar. 21, 2007, the disclosures each of which are expressly incorporated herein by reference. This application is related to the National Stage filing of PCT International Application Serial No. PCT/IB2008/000619, filed Mar. 20, 2008, which claims the benefit of European Application Serial No. EP 07 005 761.7, filed Mar. 21, 2007, the disclosures each of which are expressly incorporated herein by reference.

The invention relates to a process for the sterilisation of liquids contained in hermetically sealed containers, and a device for carrying out the process.

BACKGROUND OF THE INVENTION

One of the sterilisation methods generally employed in industry is by autoclave, where containers are treated in packets ("batches") typically at a temperature between 90° C. and 130° C. for several minutes, at rates of several thousands of containers per hour. However, sterilisation at these temperatures can substantially alter the properties of the treated product (colour, taste, odour, biophysical, biochemical and other qualities). In a conventional thermal sterilisation process, the rise in temperature is effected slowly and allows the microorganisms to adapt and to better resist the increase in temperature.

Processes aimed at reducing the temperature threshold necessary for sterilising an aqueous liquid by application of electric fields are described in U.S. Pat. No. 4,695,472 and EP 1 328 167. The process described in U.S. Pat. No. 4,695,472 however is concerned only with the sterilisation of a flux of liquid and can not be employed for sterilisation of bottles or other containers filled with liquid. The proposed amplitude of the electric field, applied to a bottle of about ten centimeters in diameter, would require very high voltages, difficult to generate and apply homogeneously.

In EP 1 328 167, a process for the sterilisation of bottles or other containers filled with liquid is described. It is proposed to limit the sterilisation threshold temperature $T_S$ by subjecting the product simultaneously to heating by electric field and to the action of ultrasound vibrations. This technology does however prove to be ineffective in practice, on the one hand because different microorganisms have different sensibilities to ultrasound vibrations, as a function of frequency and amplitude, on the other hand because the homogeneous application of ultrasound vibrations throughout the volume of the container is difficult to achieve.

Also, with known processes of sterilisation via electroporation, it is difficult to achieve a good uniformity of treatment of hermetic containers containing liquid, due to the rapidity of heating and the form of the containers, causing disparities in temperature and electric field in the volume of liquid to be sterilised. To compensate these disparities and to ensure reliable and irreversible destruction of microorganisms throughout the volume of liquid, the average temperature and/or the amplitude or the application time of the electric field could be increased. However, the consequence of this would be increased alteration of the properties of the liquid.

During heating, the pressure inside the container increases and can be accompanied by an irreversible deformation of the container, especially with respect to bottles or other containers made of plastic materials. The advantage of processes of sterilisation by electric field is a drop in temperature and sterilisation time relative to conventional thermal pasteurisation processes. Yet there is an advantage to lowering the temperature and treatment time still further to reduce effects due to the rise in internal pressure.

Devices for pressure compensation in the field of high-temperature sterilisation of containers are described in patents GB390768, U.S. Pat. No. 2,909,436, FR1436405 and FR2035678. In these systems, the internal pressure is compensated by the pressure of the liquid surrounding the container, determined by the height of the column of liquid in which the containers are immersed. This liquid also serves to heat the content of the container, making the sterilisation process relatively slow, with negative consequences on the alteration of the properties of the food in the container. Such processes are also not intended for, nor adapted to, the sterilisation of PET bottles or other containers made of plastic of which the resistance to creep decreases sharply at conventional thermal pasteurisation temperature.

SUMMARY OF THE INVENTION

An aim of the invention is to provide a sterilisation or pasteurisation process which is efficient, effective and reliable at industrial rates of throughput, capable of sterilising or pasteurising liquids contained in hermetic containers, including containers of sizes and shapes usual in the food industry, made of plastic or other materials which do not support high temperatures. An aim is also to provide a device for carrying out such a process.

Another aim of the invention is to provide a sterilisation or pasteurisation process for sterilising or pasteurising, at industrial rates, liquids contained in hermetic containers including containers of sizes and shapes usual in the food industry, which process does not alter, or only slightly alters, the properties of the liquid.

It is advantageous to provide a process for sterilisation of a liquid which does not heat the liquid, even locally, above 70° C., preferably not above 65° C.

Another aim of the invention is to provide a device for sterilising or pasteurising liquids contained in hermetic containers of different sizes and shapes usual in the food industry. It is advantageous to provide a device which allows the treatment of liquids contained in hermetic containers at industrial rates, and at low cost.

Aims of the invention are realised by a sterilisation process according to Claim 1.

The process for the sterilisation of hermetically sealed containers containing a liquid to be sterilised, according to the present invention, comprises transport of the containers to a treatment zone where the containers are immersed in a flux of external fluid, heating in volume of the liquid to be sterilised by electromagnetic waves at a rate greater than 28° C. per second at a treatment temperature T of between 20° C. and 66° C., agitation of the container during heating of the liquid, and according to the value of the treatment temperature T, exposure of the liquid to an electric field in pulses immediately or slightly after heating of the liquid, the amplitude E of the electric field in V/cm being selected such that the equation:

$$C(T) \le \log(E+1) \le B(T)$$

is satisfied for the values:

$$B(T) = -2.340 \cdot 10^{-5} T^3 + 1.290 \cdot 10^{-3} T^2 - 3.110 \cdot 10^{-2} T + 5.0$$

$$C(T) = -4.503 \cdot 10^{-5} T^3 + 2.888 \cdot 10^{-3} T^2 - 5.900 \cdot 10^{-2} T + 4.0$$

where T is the treatment temperature in Celsius.

Highly surprisingly, the inventors found that by reheating the liquid very rapidly, at a speed greater than 28° C. per second, the electric field to be applied to destroy the microorganisms can be sharply reduced relative to known processes. Such that, at treatment temperature values of 64 to 66° C., the amplitude of the electric field can even be zero. In other words, if the liquid is heated in volume at all parts at over 28° C. per second, effective and reliable pasteurisation of the liquid does not require any exposure to the electric field, in any case for a treatment temperature over 64° C., and for lower temperatures, pasteurisation can be carried out by exposure to an electric field of amplitude much lower than conventionally proposed.

Due to the importance of the speed of heating on the efficacy of pasteurisation, uniform heating in volume is very important to ensure that the entirety of the volume of liquid is subjected to rapid heating. To this end, the liquid is agitated or turbulised and reheating in volume is conducted high-frequency waves or microwaves. Heating by HF waves or microwaves makes it possible to obtain heating by agitation of the water molecules, on minimising ohmic heating by electric current, to avoid "pinch" effect problems causing non-uniform heating. The frequencies of this radiation are preferably more than 1000 kHz.

The electric field for treatment by electroporation is preferably alternating and supplied by pulses, the frequency of the alternating field preferably being between 100 kHz and 1000 kHz.

For the majority of microorganisms representing a danger for food products and especially beverages, but also for pharmaceutical and medical products, the mechanism of adaptation of the microorganism to a rise in temperature is not realised at heating speeds of over 28° C. per second throughout the heating process.

Thermal stresses on the membranes of the microorganisms due to the very rapid rise in temperature of the liquid add to the stresses due to the effects of the alternating electric field, the frequency of which is selected to oscillate the effects of stress on the membranes and consequently amplify the local maximal stresses which these membranes undergo. This combination allows a better concentration of the energy of the electric field on destruction of the microorganisms by electroporation, by minimising the loss of electric energy in heat and therefore the electric power necessary for irreversible destruction of the microorganisms. This allows the treatment of larger volumes and more easily avoids problems of breakdown and local heating which can the properties of the liquid to be sterilised.

The total calorific energy supplied to the liquid to be treated by said electric field pulse(s) can advantageously be very low, especially less than 0.05 J/cm$^3$.

An advantage of the present invention is therefore to be able to carry out very rapidly and at temperatures under 66° C., with a relatively weak electric field, even zero, irreversible operations of destruction or collective electroporation on cells found in large quantities in an aqueous solution, in particular inside a hermetically sealed container. In this case, it has proven possible to carry out irreversible destruction of microorganisms, such as moulds and yeasts in the vegetative state and in the form of spores, at temperatures not exceeding 65° C., for treatment times not exceeding one to two seconds.

This enables long-term, effective sterilisation of water-based products or those containing water, particularly drinks (such as flat mineral waters, flavoured waters, tea, fruit juices and derived products, milk and derived products, beer) enclosed in containers made of plastic materials, notably PET, of which the maximum temperature for thermal stability is of the order of 70° C.

Heating in volume can be done by high-frequency electromagnetic waves or microwaves. A flux of heated fluid flowing around containers improves the obtaining of an uniform temperature field inside the container, by way of convective thermal exchange. Further, by raising the static pressure progressively with the heating of the container and its contents, it enables compensation of the increase in pressure inside the container associated with heating of the product, and consequently prevents plastic deformation of the container.

Rapid heating in volume of the product enclosed in the container creates disparities in temperature due to the fact that the dielectric properties of the material of the container are substantially different to those of the product containing water. This means that the density of power developed in the product is even greater than that developed in the material of the container. At heating speeds over 30° C. per second, the differences in temperature can reach more than 10° C., and the gradients more than 1,000° C. per centimeter. The non-uniformities are amplified in the thickened zones of the wall of the container, for example the neck and the bottom of the bottle. It is in these places where there can be a risk that the sterilisation process is incomplete.

Given that heating of the walls takes place almost only by thermal conduction and by convection, non-uniformities in the temperature field are reduced by intensifying heat exchanges by thermal conductivity and by convection, on the one hand by agitating the container during heating, and on the other hand by immersing the container in an external fluid flux (liquid or gas) heated to a temperature equal to or slightly higher (for example from 1 to 2° C.) than that desired for the liquid inside the container.

The relative speed of the fluid flux relative to the containers determines the intensity of the heat flux of the fluid to the container and the local difference in temperatures between the liquid and the wall of the container containing it. For example, by immersing ½-liter PET bottles filled with tea in a water flow at 67° C., on heating them by microwaves at 28° C. per second from 20° C. to 65° C. (on average), for a speed passage of the bottles in the sterilisation station of 0.42 meter per second and a water flow speed at 67° C. of 1.2 meter per second, a uniform temperature field (+/−0.5° C.) was obtained in close to one second.

Preferably, the fluid flux in which the containers are immersed is turbulised, which simultaneously agitates the containers.

Advantageously, the same sterilisation station can be used to heat the content of the containers and the external liquid flux.

Preferably, the alternating electric field is applied after a pause of the order of one to two seconds following the heating step. This pause serves to uniformalise temperatures by thermal conductivity and by convection. In the sterilisation process according to the invention, heating of the liquid can take place simultaneously with the electric field pulse or pulses.

It is advantageous to space the action zone of the thermal pulse from that of the electric field pulse. For example, a transit zone can be inserted in between the two, where the electric field is zero or negligible and where the temperature field evens out in the volume of the liquid such that the difference of temperature between the central and peripheral parts of the liquid does not exceed one degree. The liquid to be treated passes through this transit zone during the pause mentioned above between heating of the liquid and application of the electric field.

BRIEF DESCRIPTION OF THE SEVERAL VIEWS OF THE DRAWINGS

Other aims and advantageous characteristics of the invention will become evident from the claims and detailed description presented below, by way of illustration, with reference to the attached drawings, in which:

FIG. 1 shows a graph illustrating the relation between the treatment temperature and the amplitude of the electric field according to the invention;

FIG. 2 shows a graph illustrating electric field pulses according to the invention;

FIG. 3 shows a device for carrying out a sterilisation process according to an embodiment of the present invention;

FIG. 4a shows an electric field distributor device according to a first embodiment; and FIG. 4b shows an electric field distributor device according to a second embodiment;

FIG. 5 shows a device for carrying out a sterilisation process according to another embodiment of the present invention;

FIG. 6a shows part of the conduit comprising a seal device (here in a case of bottles having a noncircular cross-section);

FIG. 6b is a sectional view along the line A-A of FIG. 6a; and

FIG. 7 is a sectional view of a part of a transport conduit for containers, according to one variant of the invention;

FIGS. 8a to 8g show schematically the path taken by hermetically sealed containers in a device for carrying out a sterilisation process according to alternative embodiments of the present invention.

DETAILED DESCRIPTION OF THE INVENTION

Figure 6C:
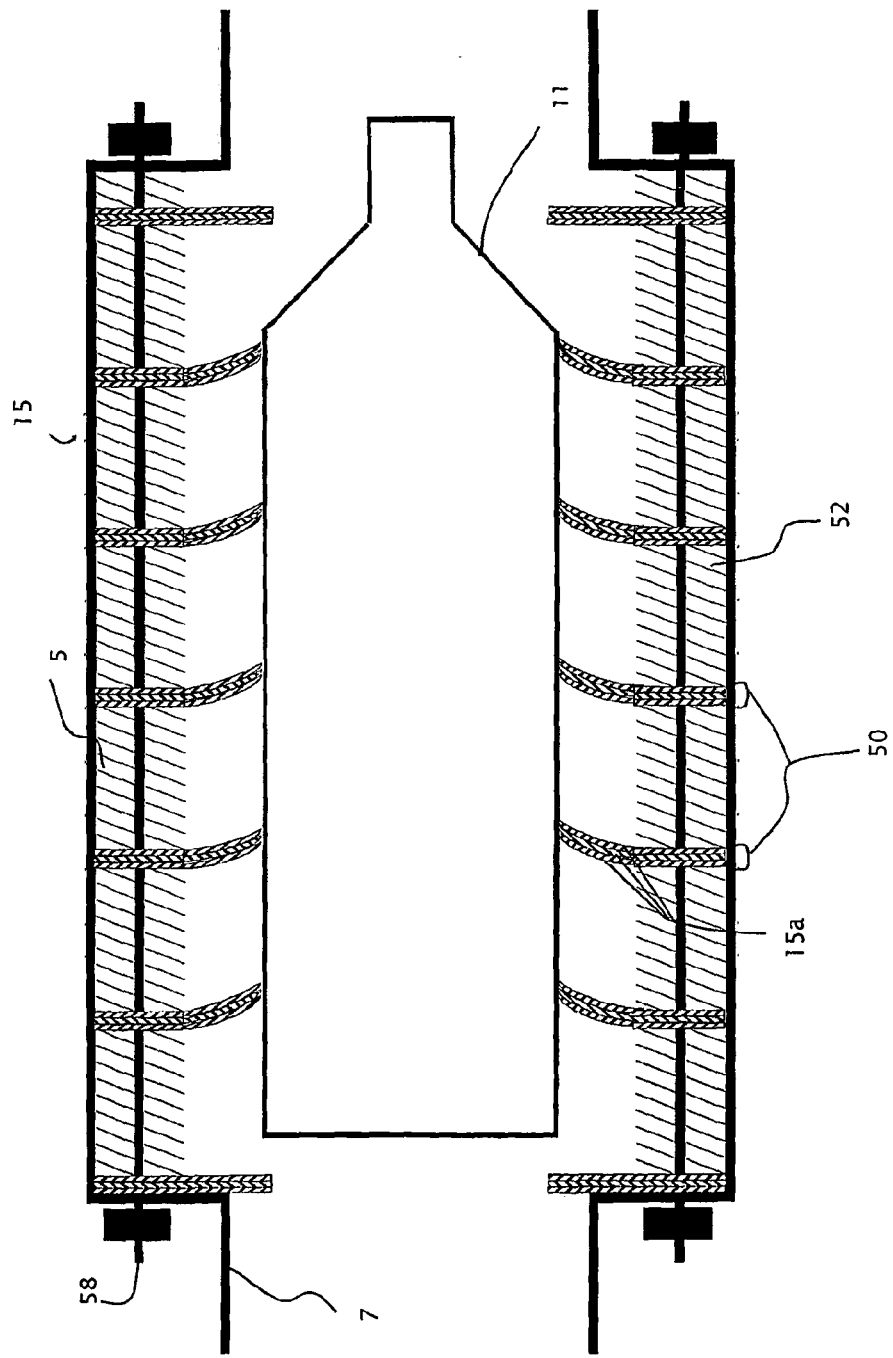
FIG. 6c shows part of the conduit comprising a seal device according to an embodiment of the present invention.

The sterilisation process according to the present invention comprises the heating of the liquid to be treated by an electric field having a frequency greater than 1 MHz, at a speed greater than 28° C. per second, to a treatment temperature T of between 20° C. and 66° C. Depending on the value of the treatment temperature T, the liquid is exposed to an alternating electric field in pulses immediately or slightly after the heating of the liquid, the amplitude E of the electric field in V/cm being selected such that the empirical equation:

$$C(T) \leq \log(E+1) \leq B(T)$$

is in any case satisfied for the values:

$$B(T) = -2.340 \times 10^{-5} T^3 + 1.290 \times 10^{-3} T^2 - 3.110 \times 10^{-2} T + 5.0$$

$$C(T) = -4.503 \times 10^{-5} T^3 + 2.888 \times 10^{-3} T^2 - 5.900 \times 10^{-2} T + 4.0$$

where T is the treatment temperature in Celsius.

This relation is illustrated by the graphic of FIG. 1.

B(T) represents the upper limit of the amplitude of the electric field reasonably necessary for pasteurising or sterilising a water-based liquid under industrial pasteurisation conditions of products according to the present invention.

C(T) represents the lower limit of the amplitude of the electric field below which there is not destruction of all the typical microorganisms representing a danger for the quality and conservation of the product or to the health of the consumer or the individual.

A(T) represents the lower limit of the amplitude of electric field below which, according to the present invention, pasteurisation of a water-based product and containing typical microorganisms representing a danger for the quality and conservation of the product or the health of the consumer or of the individual does not take place.

For example, the value of the electric field necessary for pasteurising a liquid according to A(T) is:

$E \approx 0$ V/cm, when $T = 65°$ C.
$E \approx 10^2$ V/cm, when $T = 60°$ C.
$E \approx 10^3$ V/cm, when $T = 50°$ C.
$E \approx 5 \cdot 10^3$ V/cm, when $T = 40°$ C.
$E \approx 10^4$ V/cm, when $T = 30°$ C.
$E \approx 5 \cdot 10^4$ V/cm, when $T = 20°$ C.

It is evident that this relation gives only a first estimation which can be specified empirically as a function of the microorganisms (cells) to be destroyed and the properties of the liquid.

The appearance of the pulse of the alternating electric field is illustrated in FIG. 2 where the times $t_1$, $t_2$ and $t_3$ are indicated.

The oscillation of the electric field is preferably essentially sinusoidal, but can take another form.

The characteristics and the form of the pulses of alternating electric field are configured to maximise electroporation of the membranes of the microorganisms and reduce generation of electric current lost to heat. For this purpose, the period $t_1$ of an oscillation of the electric field preferably has a value $$t_1 > 1 \, \mu s (10^{-6} \text{ seconds})$$

Below this duration, the microorganisms are insensitive to the oscillations of the electric field.

For a constant amplitude of electric field, the greater $t_1$ is, the more intense are the current losses due to ohmic heating accompanying passage of the oscillating electric current through the heated medium, given the finite electrical resistivity of the medium. In the case of heating containers made of plastic filled with beverage by high-frequency currents, in order to minimise these losses, it is very advantageous to limit the frequency to 100 kHz, or $t_1$ to 10 µs, preferably to 5 µs.

This is therefore the limiting condition for $$1 \, \mu s < t_1 < 10 \, \mu s.$$

The duration $t_2$ of an oscillating electric field pulse is greater than the period $t_1$ of an oscillation of the electric field:

$$t_2 > t_1.$$

The upper value of $t_2$ is determined by total heating of the zones of thermal perturbations due to the fact that the electrical resistance of the electrolytes—drinks are a particular example—decreases with a rise in temperature. The electric current, in this case, will always be concentrated in more or less cylindrical zones oriented along the electric field vector. These zones then contract rapidly, stimulated by "pinch" effects. The temperature in these zones rises exponentially, resulting in unacceptable local heating, or even breakdown.

These stresses result in the limiting relation for $t_2$:

$$t_2 < c \cdot dT \cdot R / E^2$$

where c, dT, R, E are respectively specific heat, limit temperature gap, resistivity of the medium, and amplitude of the electric field.

Given the experimental fact that the electrical resistivity of an aqueous medium such as a drink does not exceed 10 Ohm·m and that c=4 megajoules/m³·degree, for dT<0.5 degrees and E=1000 kV/m, there is:

$$t_2 < 20 \, \mu s.$$

The duration $t_3$ is the time lapse between two pulses of electric field. It is preferably greater than the time of compensation of the ohmic heating perturbations by the pulses of hydrodynamic turbulence.

If v is the characteristic speed of hydrodynamic instabilities and L is their amplitude, the compensation condition is:

$$t_3 > L/v$$

For the case of pasteurisation of sealed bottles filled with drink, according to the present invention, there is L>0.003 m and v<1 m/s, giving $t_3$>0.001 s.

The upper limit for $t_3$ is given by the condition of having at least one pulse per treated container. In this case $t_3$<LL/vv, where LL is the characteristic dimension of the container in the direction of its movement across the electric field, and vv its speed.

For a typical case of pasteurisation of bottles of 0.5 l, LL=0.3 m and vv>1 m/s, there is:

$$t_3 < 0.3 \text{ s}$$

If a liquid flow $t_3$<LLL/vvv is treated where LLL is the length of the zone of application of the electric field and vvv is the speed of flow through this zone.

For a typical case where LLL=0.3 m and vvv>1 m/s, there is:

$$t_3 < 0.3 \text{ s}$$

In the sterilisation process according to the invention, heating of the liquid can take place simultaneously with the pulse or pulses of electric field. In practice, it is more advantageous to first subject the liquid to the heating pulse, and to then apply the pulse or pulses of electric field. This pause is useful for better evening out the temperature field in the liquid to be sterilised such that all the zones of the liquid, including those of the layers bordering the liquid-solid interfaces of the container, acquire essentially the same temperature prior to application of the electric field.

If x is the characteristic thickness of the boundary layer (at most 0.3 mm), the pause duration $t_p$ is preferably greater than:

$$t_p = (d \cdot c \cdot x^2)/z$$

where d, c and z are respectively the density, thermal capacity and thermal conductivity of the liquid to be sterilised. For the majority of applications the duration of this pause does not exceed 1 or 2 seconds.

For some applications it is advantageous to space the zone of action of the thermal pulse from that of the electric field pulse. For example, a transit zone can be inserted in between the two, where the electric field is zero or negligible and where the temperature field evens out in the volume of the liquid such that the difference in temperature between the central and peripheral parts of the liquid does not exceed one degree. The liquid to be treated passes through this transit zone during the pause mentioned earlier between the heating of the liquid and the application of the electric field.

FIGS. 3 and 5 schematically illustrate devices for carrying out the process according to different embodiments of the present invention.

The device 1 comprises a transport system 2 of the liquid to be treated 3, a station for the heating in volume 4 of the liquid to be treated and a station for application of an electric field in pulses 5.

The transport system 2 comprises an inlet station 6, a transport conduit 7, and an outlet station 8. The containers can be guided by a standard conveyor 33 and deposited onto a bucket chain (or any other equivalent mechanism) in a column part 7a of the conduit 7.

The transport system can also comprise a pumping system 9a, 9b, for circulation of the transport liquid 10 in which hermetic containers 11 containing the liquid to be treated 3 are immersed. The transport system can advantageously include a hot circuit 12a and a cold circuit 12b, each fitted with a system for pumping 9a, 9b and for recirculation of the transport liquid. The hot circuit transports the containers across the heating and electric field application stations and returns the transport liquid via a return conduit 13a to the transport conduit 7 in the proximity of the inlet station. The cold circuit 12b also has a pumping system 9b and a return conduit 13b interconnecting with the transport conduit 7 between a position in the proximity of the outlet station 8 and an interface 14 separating the hot and cold circuits.

The interface 14 advantageously comprises one (or more) seal devices 15 (see FIGS. 6a and 6b) comprising a plurality of flexible and elastic walls 15a juxtaposed in a section of the conduit 7, for example made of rubber, comprising openings 15b and a plurality of juxtaposed flexible walls (15a) having central openings designed to fit to the profile of the container to be treated when they are deformed. In this way, the containers participate in creating sealing between the hot and cold circuits.

The walls 15a advantageously comprise a plurality of petals 54 which can deform freely, advantageously between 6 and 12 petals, for example around 8 petals, allowing the wall to easily fit to all irregularities in form and/or dimensions of the container. The petals can be formed by axial slots 55 in an annular wall, or otherwise by a plurality of distinct pieces.

The central opening 15b of the walls is advantageously substantially circular in shape, allowing the wall to easily fit to different profiles of containers to be treated. In this way it is not necessary to adapt the form of the walls to the external shape of the container. The diameter of the central opening is advantageously less than the minimum dimension of the smallest transversal section of the body of the container, thus ensuring maximum sealing of the seal.

A seal device according to one embodiment of the invention is shown in FIG. 6c. In this variant, the seal device 15 comprises several groups 50 of flexible and elastic seal walls 15a, spaced over the length of the seal device 15 in the conduit 7. Each group 50 of walls comprises a plurality of flexible seal walls 15a (see FIGS. 6d and 6e), advantageously between 2 and 6 walls, preferably 3 or 4. The walls 15a of a group of seal walls 50 are fixed, one to the other, by their periphery to the enclosure in which the container moves and can be distanced from one another by separating rings 51 made of metal, or some other rigid material. Advantageously the distance between the walls in a group 50 is comparable to the thickness of the walls, for example of the order of 0.5 mm to 3 mm, for example around 1 mm. This space between the walls makes free movement of the flexible lower part of the walls 15a easy.

Figure 6D:
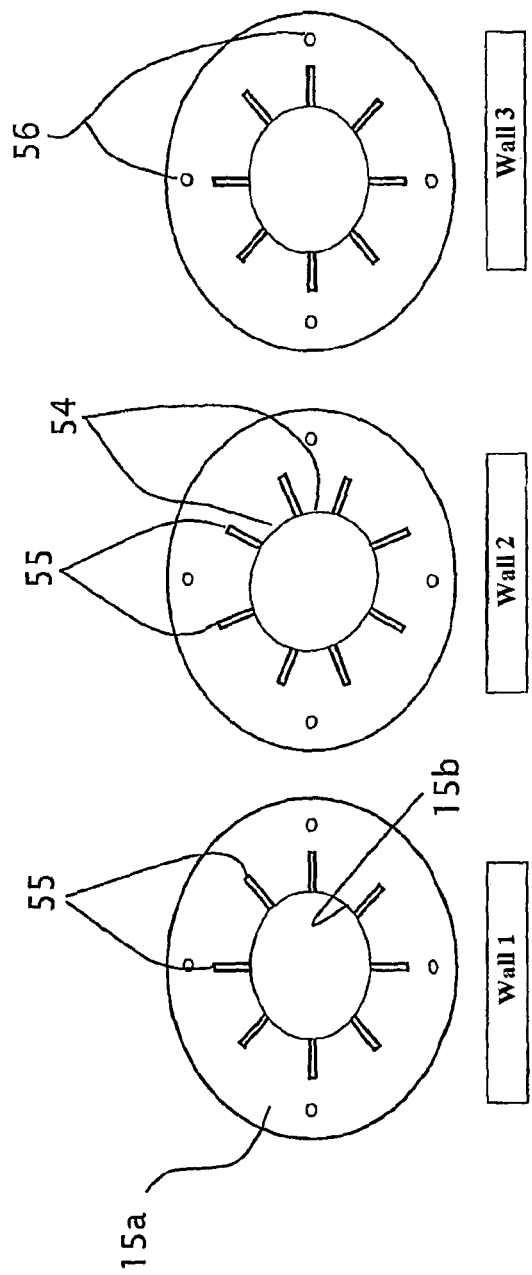
FIG. 6d shows walls of a seal device according to an embodiment of the present invention.
Figure 6E:
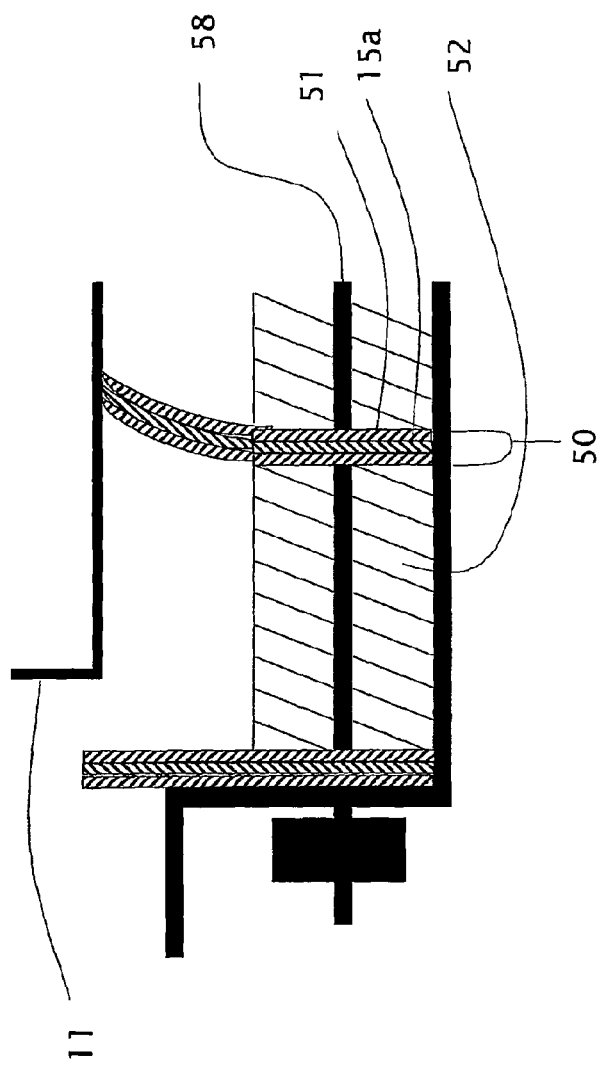
FIG. 6e shows part of a seal device according to an embodiment of the present invention.

The flexible walls of a group of seal walls 50 are shifted radially relative to the adjacent walls, such that the petals 54 of a wall (see the wall 2 of FIG. 6d) are shifted radially relative to the petals 54 of the adjacent walls (see the walls 1 and 3 of FIG. 6d). In a preferred embodiment the walls are shifted radially, relative to the adjacent walls, such that the slots 55 forming the petals 54 are positioned at a maximal distance in the azimuthal plane, relative to one-another. When a container passes through the flexible walls of a group of walls 50 the container causes curving of the petals which fit to the form of the transversal section of the container. The petals of the walls are compressed against the surface of the container by the pressure of the liquid in the conduit, as well as by the forces generated by the flexion of the petals. As the slots forming the petals do not coincide, the walls of one group 50 pressed tightly against each other, against the surface of the container, offer a very high hydrodynamic resistance. Accordingly, the petals of the grouped walls form an effective seal between the container and the wall 15a, preventing movement of transport liquid 10 through the seal device and at the same time minimising resistance to movement of the containers along the conduit.

The hydrodynamic resistance constituted by the petals of the walls pressed against each other, against the surface of the container, increases with the increase in total pressure difference between the fluids on the opposite sides of the device of the seals (inlet and outlet of the device in the conduit 7) and the elasticity forces of the petals. Therefore, the effect of sealing is self-regulated, which is not the case for conventional seals.

In the variant shown in FIG. 6c the seal device can advantageously comprise at least 3 groups 50 of flexible and elastic seal walls 15a, for example between 3 and 20 groups of walls, preferably between 5 and 10 groups of walls. The groups 50 of flexible and elastic walls are separated by separators 52, for example in the form of a ring made of metal or other material, and are held in place by a bolt 58 or other fixing mechanism. The distance between two groups of walls can be advantageously between 5 mm and 40 mm, for example between 5 mm and 20 mm.

This configuration of the seal devices, with several groups of flexible seal walls 15a, spaced over the length of the seal device 15, ensures proper sealing between the hot and cold circuits, even for containers having a transversal cross-section varying over the length of the container, whilst at the same time allowing easy movement of the containers along the conduit.

Further, the flexible and elastic walls comprising a plurality of petals automatically fit to all irregularities in shape and dimension of the containers, and ensures proper sealing of the seal for any container profile, for example containers with different forms such as round, oval, square, polygonal or other form, even forms without axial symmetry, or containers with a non-uniform transversal cross-section over the length of the container (for example conical, undulating form, figures in relief).

Advantageously, the seal devices of the invention can be used with different containers, having different shapes, without the need to change the system of seal walls for each shape of container.

The seal device of the invention is simple, effective, and can be made at low cost.

Of course, the seal device can be inserted at any place along the transport conduit, and enables the separation of zones of the conduit. The seal device can also separate zones of liquid having totally different pressures or separate zones of the conduit containing different fluids, for example forming a separation between a gas such as air and a pressurised liquid, or between two different liquids.

Seal devices 15 can also be placed in other places along the transport conduit 7, for example upstream of the heating station 4.

The cold and hot circuits can also comprise heat exchangers 31, 32 on the return conduit, for recovering heat from the transport liquid and/or from the liquid to be treated.

The cold circuit allows the temperature of the liquid to be treated to be rapidly lowered in order to preserve the properties of the liquid and, if necessary, to reduce problems of deformation of containers made of plastic.

The heating station 4 comprises a system for generating thermal pulses 35 fed by a thermal energy generator 37. The thermal generator can be, for example, in the form of a generator of high-frequency electric fields operating at a frequency greater than 1 MHz or a microwave generator. The energy is transferred from the generator 37 to the system 35 by means of a coaxial cable or a waveguide 16. It is possible to provide several generators arranged in a juxtaposed manner along the transport conduit 7.

The station for application of an electric field 5 comprises a bipolar oscillating electric field pulse distributor 17 connected to a bipolar oscillating electric field pulse generator 18 by means of a coaxial cable 19. It should be pointed out that, as mentioned earlier, for treatment temperatures over 64° C., it is possible to do without the electric field application station.

The thermal pulse 4 and electric field application stations 5 are separated by a thermally insulated transit section of the conduit 20, creating a pause between thermal treatment and electric pulse treatment. This pause advantageously enables uniform distribution of the temperature field in the liquid to be treated and on the surfaces of the solid bodies on contact therewith.

In the embodiment of FIG. 3 the liquid to be sterilised is contained in containers 11 immersed in a transport liquid 10 flowing in the conduit 7 for transporting the containers. The containers can for example be plastic bottles, filled for example with a drink or liquid foodstuff.

It is also possible to transport the containers containing the liquid to be sterilised via a heating station and a station of application of the electric field by means other than liquid in a conduit, for example by a pressurised gas flow in a conduit (the pressure of the gas being selected so as to compensate the pressure inside the container, thus avoiding any deformation of the container due to heating) or by a mechanical transport mechanism such as a conveyor system. However, a transport system by fluid has the advantage of enabling a good uniformity in temperature distribution around the container during heating and during the pause prior to application of the electric field. The use of a transport liquid having dielectric properties similar to those of the liquid to be sterilised advantageously allows good control of the heating of the liquid to be sterilised as well as of the application of the local electric field in the liquid to be sterilised.

The containers, made of dielectric material, can be in the form of rigid containers, such as bottles made of glass or plastic (for example PET or other polymers).

One or more agitation devices 21 can be added to the system to agitate the transport liquid and the containers located in the transport liquid. In one variant, the agitation device comprises one or more jets (nozzles) (not illustrated) arranged on the wall of the conduit and opening into the interior of the conduit, for injecting a fluid to create turbulence in the transport fluid flowing in the conduit, thus evening out the temperature field in the liquid. Containers transported in the conduit can also be agitated or rotated, for example by the control currents in a vortex flow in the transport liquid, in order to uniformalise the liquid to be treated inside the containers. Agitation devices 21 can also be placed in the cold circuit part 12b to accelerate cooling of the liquid in the container after sterilisation or pasteurisation treatment.

Tubes made of dielectric material (quartz, for example) 22 are mounted in the conduit to ensure the passage of the electric field serving for the heating of the liquid inside the conduit.

Temperature sensors 23 are arranged all along the conduit for measuring the temperature of the liquid at the inlet of the station for generation of thermal pulses, in the heating zone, at the outlet of this zone and the outlet of the transit section 20 of the conduit.

An electric field sensor 24 is arranged in the zone of application of the electric field.

In one embodiment of the device, a mechanism is provided to ensure variable displacement speed of the solid bodies as they pass through the conduit, for example by changing the cross-section (diameter) of the conduit to vary the speed of the flux of the transport liquid.

A distributor device of electric field, according to a first variant, is shown in FIG. 4a. In this variant, the distributor comprises electrodes 25a, 25b located on either side of the conduit to ensure the passage of pulses of alternating electric field of frequency between 100 kHz and 1000 kHz transversally through the conduit 7 (FIG. 3), as illustrated by the field lines 26.

In particular, the electric field passes from the upper electrode 25a to the lower electrode 25b, the two electrodes being installed inside a tube 27 (made of quartz, for example), hermetically integrated in the conduit. The distance <<a>> between the electrodes can be optimised empirically to ensure the best possible uniformity of the transversal electric field in the volume of the containers 11. If the distance a is for example of the order of 4 cm, then to get an effective amplitude of electric field of 1-3 kV/cm, there must be a difference in potential between the electrodes of the order of 400-1200 kV.

FIG. 4b illustrates an electric field distributor device according to a second variant. In this variant, the pulses of the electric field are created by an induction system and the electric field lines 26' are essentially longitudinal. The conduit 7, filled with water as transport liquid 10 transporting containers 11, such as bottles containing a liquid to be sterilised, passes through a body of the induction system 25. The electric field distributor device is fitted with a core 28 and one or more primary windings 29 attached to a feed via connections 30a, 30b. The quantity of primary windings can be determined empirically, for example by measuring the electric field present in the transport liquid.

In the embodiment of FIG. 3, the containers 11 are immersed to a depth H in a column part 7a of the transport conduit 7 filled with transport liquid 10.

The column of transport liquid exerts an external pressure which tends to compensate the internal pressure during heating of the liquid to be treated according to formula (2) which determines the height H of the column corresponding to the temperature $T>T_1$.

$$H \times d \times g = (T_2/T_1) \times P_1 - C + V_P + V_S \quad (2)$$

where:
"H" is the height of the column of liquid in which the containers to be treated are immersed;
"d" is the density of the external liquid;
"g" is the local acceleration of gravity;
"$P_0$" is the initial pressure of the compressible liquid in the container on entry into the device;
"$V_S$" is the difference between the saturated vapour pressure of the incompressible liquid at temperatures $T_2$ and $T_1$. For water, at $T_1=20°$ C. for example, the saturated vapour pressure is minimal and, $V_S$ is practically equal to the saturated vapour pressure of water at temperature $T_2$. For example, if $T_2=65°$ C., then $V_S=0.25$ bar;
"C" is equal to $(k \times V_V)$ where k is the coefficient of volumic elasticity of the material of the container at temperature $T_2$ and $V_V$ is the volumic deformation;
"$V_P$" is the variation of internal pressure due to variation in saturation of the incompressible liquid by the compressible liquid. $V_P$ is measured in a non-deformable container (for example made of glass) of the same form and volume as the treated container, as the difference in pressure between the real manometric pressure at temperature $t_2$ and pressure $P_2=P_0 \times (T_2/T_1)$. For drinks not saturated in $CO_2$, such as for example flavoured water or milk, $V_P$ is close to zero. Compensation is total when C=0.

The depth H can be decreased by increasing the density d of the external liquid medium in which the containers are dipped. In particular, solid bodies of small dimension p (p must be much smaller than the characteristic dimension of the container) but of a density greater than that of the liquid, for example in the form of powder, can be added to this liquid. This measure will be effective only when the pressure exerted by the solid bodies is equal in all directions. For this, the solid bodies have to be provided with chaotic movement of which the average speed is greater than the square root of gp, where:
"g" is the local acceleration of the gravity
"p" is the dimension of the solid bodies
and their specific quantity n (quantity of solid body per unite of volume) corresponds to the desired increase in density d.

To satisfy this condition, the force of gravity of the solid body of mass m, i.e. mg, must be less than the force F exerted by this body on any wall due to its inertia. If v is the speed of chaotic movement, the following order of magnitude can be obtained for F: $F=m \times (v/t)$, where $t=d/v$, then $F=(mv^2)/d$. It is therefore necessary that $F>>mg$, therefore that $v>>(gd)^{(1/2)}$.

If bottles are treated sequentially and in the direction of their length, one behind the other, a ram 34 sends the bottles in the horizontal part of conduit 7c.

Once they are mounted in the outlet column part of the conduit 7b, the containers can be discharged by a ram or other mechanism onto a conveyor 33.

In the variant illustrated in FIG. 7, the transport conduit 7' is in the form of a tube configured for inserting bottles in the direction of their lengths into the inlet part 7a' of the conduit, and for guiding them to the outlet of the conduit in the cold circuit part. To this effect, the tube has radii of curvature large enough to ensure transition between the vertical and horizontal parts of the conduit. The circulation of the transport liquid in the direction of movement of the containers facilitates the movement of the containers along the conduit, not only due to the pressure exerted in the direction of movement, but also due to the lift (Archimedes force) and lubrication created by the presence of liquid around the containers.

FIGS. 8a to 8g schematically illustrate variants of the transport system 2 of the device for carrying out the process according to different embodiments of the present invention.

In the variant illustrated in FIG. 8a, the containers 11 are guided by a standard conveyor 33, and are brought up to the inlet 41 of the transport conduit 7 by a standard elevator system 40, for example a bucket chain, or any other equivalent mechanism. The containers are pushed inside the vertical column 7d of the transport conduit 7 by a friction device, for example rollers, or other ram system (not illustrated). The containers enter the transport conduit and are immersed in the transport liquid 10 flowing in the conduit 7 and progress through the transport conduit 7, pushed by one another in the direction of their length. The containers are discharged from the outlet column 7e of the conduit 7 by another friction device, for example rollers, or other ram system or equivalent mechanisms (not illustrated) designed to regulate, even slow down, the flow of containers towards the outlet of the conduit 43, and are placed onto a discharge conveyor 33.

Figure 8B:
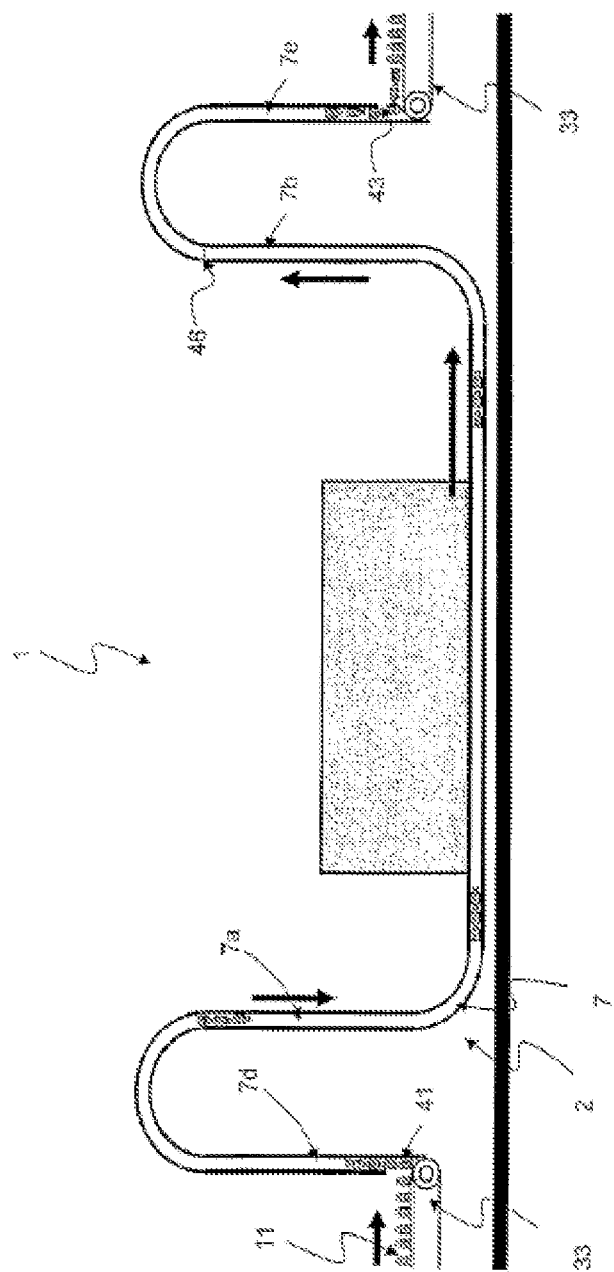

In the variants illustrated in FIGS. 8b to 8c, the containers 11 containing liquid to be treated arrive directly at the inlet 41 of the transport conduit 7 on the conveyor 33. The containers are pushed inside the transport conduit 7 by a friction device, for example rollers, or other ram system or equivalent mechanism, located at the inlet 41 of the transport conduit (not illustrated). The containers enter the first vertical part 7d of the transport conduit in the direction of their length, one behind the other, and rise up to the top of the vertical part 7b of the conduit, pushed by the force developed by the friction device or other ram system at the inlet 41 of the conduit.

The first vertical part 7b of the conduit is advantageously lubricated, for example by one or more jets (nozzles) (not illustrated), arranged on the wall of the conduit and opening into the interior of the conduit, for injecting fluid, generally water, into the interior of the conduit to reduce friction between the containers and the wall of the conduit and facilitate movement of the containers. Advantageously, the jets are oriented tangentially up the column part 7d of the conduit. The orientation of the water jets towards the top of the column 7b turns the containers round and forces them towards the top of the column 7b against the force of gravity, facilitating the vertical movement of the containers in the column 7d.

At the outlet 43 of the transport conduit 7, another friction device, for example rollers, or another ram system or equivalent mechanism (not illustrated) discharges the containers from the conduit onto a conveyor 33.

The vertical columns of the transport conduit 7a and 7b are filled with transport liquid to a level 46 defined by the parameters of the system. The presence of an extended outlet part of the conduit 7e allows increased cooling of the liquid in the containers.

Advantageously, the vertical part of the outlet conduit 7e comprises one or more jets (nozzles) (not illustrated) arranged on the wall of the conduit and opening into the interior of the conduit for injecting a fluid, generally water, into the conduit to reduce friction between the bottles and the conduit. Advantageously, the jets are oriented against the direction of movement of the containers in the part 7e of the conduit. The jets of liquid oriented against the direction of movement of the sealed containers slow movement of the containers towards the outlet 43 of the conduit, thus reducing the braking force that needs to be exerted by the friction device or ram system at the outlet 43 of the conduit.

A variant of the transport system of FIG. 8b is illustrated in FIG. 8c. In this alternative form of the transport system 2, the positioning of the inlet 41 and the outlet 43 of the conduit makes it possible to reduce the overall size of the device, which is useful for some industrial applications of the device.

In the variant of the transport system 2 illustrated in FIG. 8d, the inlet 41 of the transport conduit 7 is on a substantially horizontal part of the conduit 7f. The containers 11 arriving at the inlet of the conduit 41 on a conveyor 33 are turned on their side by a standard handling device (not illustrated) and enter the horizontal part 7f of the conduit in the direction of their length.

A variant of the transport system shown in FIG. 8d is illustrated schematically in FIG. 8e. Other variants of the transport system of the device for executing the process of the invention are illustrated schematically in FIGS. 8e, 8f and 8g. In the variants of transport systems shown in FIGS. 8f and 8g, the outlet conduit 7e is extended to allow a longer cooling period of the liquid contained in the containers before the containers exit the device.

The transport fluid can however also be pressurised gas, separated from the environment from which the containers come via two mechanical airlocks or by two airlocks wherein the pressure varies progressively to compensate the differences in internal and external pressure and to thus eliminate deformation of the container, especially during cooling of the liquid in the containers. In summary, in this particular case, the immersion zones of height H and density d are replaced by airlocks which provides the passage of the containers from the environment from which they come to a pressurised zone, this pressure $P_x$ being equal to the internal pressure $P_i$ developing in the containers during heating.

In reference to the embodiment of FIG. 5, the height of the vertical column part of the conduit in order to compensate the pressure developed in the container during heating can be reduced by generating pressure in the part of the conduit 7c passing through the treatment stations 4, 5 and the cooling circuit, by pumps 36a, 36b injecting gas or transport liquid into said part of the conduit 7c. Seal devices 15 such as described above are placed on either side of the pressurised section of the conduit 7c.

Manometers can be placed on the whole circuit to control pressure in the conduit, and purge valves can also be provided for eliminating air from the system or evacuating liquid from the conduit.

Mechanical airlocks allowing the passage of the containers and separating a zone of liquid external to the container, which is heated, from a zone where this liquid is cold, or any other system of airlocks or classic system serving as a barrier to pressure but allowing the containers to pass, can replace the seal devices 15.

EXAMPLES

1. Decontamination of sealed 0.5 l PET bottles filled with freshly squeezed orange juice and contaminated with "*Byssochlamys nivea*" microorganisms. Treatment was carried out on a device of the type illustrated in FIG. 3:
   Initial concentration of microorganisms: from 3.6 to 4.2× $10^5$ unit/ml;
   Quantity of bottles treated for each cycle: 10;
   Initial temperature: 20° C.;
   Duration of treatment: 3 s (passage through horizontal conduit);
   Heating: microwave 1 GHz, power 180 kW (35° C./s) and 45 kW (9° C./s);
   Application of the electric field:
      Frequency of oscillation of the electric field: 180 kHz;
      Duration of a batch of oscillations: ca. 0.02 ms;
      Frequency of batches of oscillations: 15 Hz;
      $t_1$=6 µs, $t_2$=20 µs, $t_3$=0.05 s;
      Quantity of pulses: 12 for 180 kW and respectively 35 and 48 pulses for 45 kW;
   Productivity, linear speed of bottles: 0.4 m/s for 180 kW and 0.1 m/s for 45 kW. Length of the field application zone: 0.3 m; duration of the application of electric field pulses: 0.75 s;
Results:

| Electric field (V/cm) | Speed of temperature growth °C./s | Treatment temperature in °C., +/−1° C. | Residual concentration after tests (unit/ml) | Residual concentration 2 months after tests (unit/ml) |
| --- | --- | --- | --- | --- |
| 0 | 9 | 80 | <1 | <1 in 80% of cases |
| 0 | 9 | 65 | from 5 to 20 | — |

-continued

| Electric field (V/cm) | Speed of temperature growth °C./s | Treatment temperature in °C., +/−1° C. | Residual concentration after tests (unit/ml) | Residual concentration 2 months after tests (unit/ml) |
|---|---|---|---|---|
| 0 | 35 | 65 | <1 | <1 in 100% of cases |
| 0 | 35 | 62 | from 120 to 1500 | — |
| 30 | 35 | 62 | <1 | <1 in 95% of cases |
| 0 | 35 | 60 | ca. $10^4$ | — |
| 100 | 35 | 60 | <1 | <1 in 100% of cases |
| 0 | 35 | 55 | ca. $3\text{-}4 \times 10^5$ | — |
| 600 | 35 | 55 | <1 | <1 in 100% of cases |

2. Selective decontamination of 0.5 l PET bottles, filled with apple juice and contaminated by *Saccharomyces cerevisiae* yeasts and *Aspergillus Niger* mould. Treatment was carried out on a device of the type illustrated in FIG. 2:

- Initial concentration of *Saccharomyces cerevisiae*: $1.2\text{-}3.1 \times 10^5$ unit/ml;
- Initial concentration of *Aspergillus niger*: $1.5\text{-}4.2 \times 10^5$ unit/ml;
- Quantity of bottles treated for each cycle: 10;
- Initial temperature: 20° C.;
- Duration of treatment: 3 s (passage through horizontal conduit);
- Heating: microwave 1 GHz, power 180 kW (35° C./s) and 45 kW (9° C./s);
- Application of the electric field:
  - Frequency of oscillation of the electric field: 180 kHz;
  - Duration of a batch of oscillations: ca. 0.02 ms;
  - Frequency of batches of oscillations: 15 Hz;
  - $t_1=6$ μs, $t_2=20$ μs, $t_3=0.05$ s;
  - Quantity of pulses: 12 for 180 kW and respectively 35 and 48 pulses for 45 kW;
- Productivity, linear speed of bottles: 0.4 m/s for 180 kW and 0.1 m/s for 45 kW. Length of the field application zone: 0.3 m; duration of application of the electric field pulses: 0.75 s;

Results:

| Electric field (V/cm) | Speed of temperature growth in °C./s | Treatment temperature in °C., +/−1° C. | Residual concentration after tests (unit/ml) Sacch. cer. | Residual concentration after tests (unit/ml) Asp. niger |
|---|---|---|---|---|
| 0 | 9 | 70 | $2.8 \cdot 10^1$ | $5 \cdot 10^2$ |
| 0 | 35 | 70 | <1 | <1 |
| 0 | 9 | 65 | $1.5 \cdot 10^3$ | $1.8 \cdot 10^3$ |
| 0 | 35 | 65 | <1 | <1 |
| 65 | 9 | 60 | $5.2 \cdot 10^1$ | $3.7 \cdot 10^1$ |
| 65 | 35 | 60 | <1 | <1 |
| 120 | 9 | 60 | 3-5 | 6-8 |
| 120 | 35 | 60 | <1 | <1 |
| 120 | 9 | 50 | $3.2 \cdot 10^4$ | $2.2 \cdot 10^3$ |
| 120 | 35 | 50 | $7.2 \cdot 10^1$ | $5\text{-}6 \cdot 10^1$ |
| 1020 | 9 | 50 | $2.7 \cdot 10^2$ | $1.0 \cdot 10^2$ |
| 1020 | 35 | 50 | <1 | <1 |
| 2540 | 9 | 45 | 3-5 | $1.1 \cdot 10^1$ |
| 2540 | 35 | 45 | <1 | <1 |

The invention claimed is:

1. A process for the sterilisation or pasteurisation of a liquid contained in a hermetically sealed container, comprising the steps of:
   - transporting the container into a treatment zone where the container is immersed in a flux of external transport fluid,
   - heating a volume of the liquid to be treated in the container at a rate greater than 28° C. per second, to a treatment temperature T of between 20° C. and 66° C.,
   - agitating the container during the heating of the liquid to be treated, and
   - depending on the value of the treatment temperature T, exposing the liquid to be treated to an electric field for treatment by electroporation immediately or slightly after heating of the liquid to be treated, the amplitude E of the electric field in V/cm being selected such that the equation:

$$C(T) \leq \log(E+1) \leq B(T)$$

is satisfied for the values:

$$B(T) = -2.340 \times 10^{-5} T^3 + 1.290 \times 10^{-3} T^2 - 3.110 \times 10^{-2} T + 5.0$$

$$C(T) = -4.503 \times 10^{-5} T^3 + 2.888 \times 10^{-3} T^2 - 5.900 \times 10^{-2} T + 4.0$$

where T is the treatment temperature in Celsius,
   wherein the electric field for treatment by electroporation alternates with an oscillation frequency of between 100 kHz and 1000 kHz, and is supplied in pulses, and a duration of application of each pulse of the electric field is between 10 and 100 microseconds; and
   wherein said process is capable of decontaminating liquids at temperatures below 66° C. in the absence of acoustic vibrations.

2. The process of claim 1, wherein the total calorific energy supplied to the liquid to be treated by said electric field pulse or pulses is less than 0.05 J/cm$^3$.

3. The process of claim 1, wherein a frequency of repetition of the electric field pulses is between 10 and 100 Hz.

4. The process of claim 1, wherein application of the electric field for treatment by electroporation is carried out after the heating step of the liquid to be treated followed by a pause during which the electric field is zero or negligible.

5. The process of claim 1, wherein the heating rate is greater than 30° C. per second.

6. The process of claim 1, wherein the transport fluid is water or a water-based liquid.

7. The process according to claim 6, wherein the transport liquid is turbulised in rotation around the container.

8. The process of claim 1, wherein static pressures developed in the treatment zone are created by pumping and airlocks systems.

9. The process of claim 1, wherein static pressures developed in the treatment zone are created by columns of liquid constituting the external fluid rising above the container treatment zone.

* * * * *